United States Patent [19]
Hillman et al.

[11] Patent Number: 6,100,075
[45] Date of Patent: Aug. 8, 2000

[54] DELTA 1-PYRROLINE-5-CARBOXYLATE REDUCTASE HOMOLOG

[75] Inventors: Jennifer L. Hillman; Neil C. Corley, both of Mountain View; Mariah R. Baughn, San Leandro, all of Calif.

[73] Assignee: Incyte Pharmaceuticals, Inc., Palo Alto, Calif.

[21] Appl. No.: 09/099,676

[22] Filed: Jun. 18, 1998

[51] Int. Cl.$^7$ ............................... C12N 9/02; C12Q 1/68; C07H 21/04

[52] U.S. Cl. ..................... 435/189; 435/6; 435/252.33; 536/23.2

[58] Field of Search ............................... 435/189, 252.33, 435/6; 536/23.2

[56] References Cited

U.S. PATENT DOCUMENTS 5,789,222   8/1998   Kelly et al. ............................... 435/191

OTHER PUBLICATIONS

Yeh, G.C. et al., "The Effect of Pyrroline–5–carboxylic Acid on Nucleotide Metabolism in Erythrocytes from Normal and Glucose–6–phosphate Dehydrogenase–deficient Subjects", *J. Biol. Chem.*, 259: 5454–5458 (1984).

Samuels, S.E. et al., "Effect of Dietary Proline on Proline Metabolism in the Neonatal Pig", *J. Nutr.*, 119: 1900–1906 (1989).

Funck, R.C. et al., "Regulation and Role of Myocardial Collagen Matrix Remodeling in Hypertensive Heart Disease", *Adv. Exp. Med. Biol.*, 432: 35–44 (1997).

Leevy, C.B., "Abnormalities of Liver Regeneration: A Review", *Digestive Diseases*, 16: 88–98 (1998).

Lee, B.S., et al., "Pirfenidone: A Novel Pharmacological Agent That Inhibits Leiomyoma Cell Proliferation and Collagen Production", *Clin. Endocrinol. Metab.*, 83: 219–223 (1998).

Sakaida, I. et al., "Herbal medicine Sho–saiko–to (TJ–9) prevents liver fibrosis and enzyme–altered lesions in rat liver cirrhosis induced by a choline–deficient L–amino acid–defined diet", *J. Hepatol.*, 28:298–306 (1998).

Lorans, G., et al., "Metabolism of Proline in a Human Leukemic Lymphoblastoid Cell Line", *Cancer Res.*, 38: 3950–3953 (1978).

Herzfeld, A. and O. Greengard, "Enzyme Activities in Human Fetal and Neoplastic Tissues", *Cancer*, 46: 2047–2054 (1980).

Cohen, S.M. and J.V. Nadler, "Proline–induced inhibition of glutamate release in hippocampal area CA1", *Brain Res.*, 769: 333–339 (1997).

Cohen, S.M. and J.V. Nadler, "Proline–induced potentiation of glutamate transmission", *Brain Res.*, 761: 271–282 (1997).

Matsuzawa, T. et al., "Disease of Ornithine–Proline Pathway: A $\Delta^1$–Pyrroline–5–Carboxylate Reductase Deficiency in the Retina of Retinal Degeneration Mice", *Adv. Exp. Med. Biol.*, 153: 361–370 (1982).

Delauney, A.J. and D.P.S. Verma, "A soybean gene encoding $\Delta^1$–pyrroline–5–carboxylate reductase was isolated by functional complementation in *Escherichia coli* and is found to be osmoregulated" *Mol. Gen. Genet.*, 221: 299–305 (1990).

Dougherty, K.M. et al., (Direct Submission), GenBank Sequence Database (Accession M77836), National Center for Biotechnology Information, National Library of Medicine, Bethesda, Maryland, 20894, (GI 189497; GI 189498).

Merrill, M.J. et al., "Purified Human Erythrocyte Pyrroline–5–carboxylate Reductase", *J. Biol. Chem.*, 264: 9352–9358 (1989).

Fleming et al., "Pyrroline–5–carboxylate in human plasma," Metabolism: Clinical and Experimental, vol. 33, No. 8, pp. 739–742, Aug. 1984.

Shiono et al., "Purification and characterization of rat lens pyrroline–5–carboxylate reductase," Biochim. Biophys. Acta, vol. 881, No. 1, pp. 72–78, Mar. 19, 1986.

Chilson et al., "Pyrroline–5–Carboxylate Reductase in Soybean Nodules—Isolation, Partial Primary Structure Evidence for Isozymes," Arch. Biochim. Biophys., vol. 288, No. 2, pp. 350–357, Aug. 1991.

Dougherty et al., "Cloning Human Pyrroline–5–Carboxylate Reductase cDNA By Complementation in *Saccharomyces cerevisiae*," J. Biol. Chem., vol. 267, No. 2, pp. 871–875, Jan. 15, 1992.

Williamson et al., "Molecular cloning and evidence for osmoregulation of the DELTA1–pyrroline–5–carboxylate reductase (proC) gene in pea (*Pisum sativum* L.)," Plant Physiol., vol. 100, No. 3, pp. 1464–1470, 1992

*Primary Examiner*—Robert A. Wax
*Attorney, Agent, or Firm*—Incyte Pharmaceuticals, Inc.

[57] ABSTRACT

The invention provides a human delta 1-pyrroline-5-carboxylate reductase homolog (P5CRH) and polynucleotides which identify and encode P5CRH. The invention also provides expression vectors, host cells, antibodies, agonists, and antagonists. The invention also provides methods for diagnosing, treating or preventing disorders associated with expression of P5CRH.

12 Claims, 7 Drawing Sheets

```
           11           20           29           38           47           56
5' GCGCCC ATC AGC CGC CCG GGA GAT ATC CGC CGG GGG AGA ATA GGG TTG CAC CAT CCC 65           74           83           92          101          110
   AGA AGC TGC TGT TAG CTC GCC GGT CCT CGG CAC GCC GCC CGT TCG CCC CTG CGC 119          128          137          146          155          164
   TGT CCG CCC TTC CCC TAG CGT TAC TTC CGG TCC CTC GCT GAG GGG GTT CGT GCG 173          182          191          200          209          218
   GCT CCC AGG AGG CGT GAA CCG CGG ACC ATG AGC GTG GGC TTC ATC GGG GCC GGC
                                            M   S   V   G   F   I   G   A   G 227          236          245          254          263          272
   CAG CTG GCC TAT GCT CTG GCG CGG GGC TTC ACG GCC GCA GGC ATC CTG TCG GCT
    Q   L   A   Y   A   L   A   R   G   F   T   A   A   G   I   L   S   A 281          290          299          308          317          326
   CAC AAG ATA ATA GCC AGC TCC CCA GAA ATG AAC CTG CCC ACG GTG TCC GCG CTC
    H   K   I   I   A   S   S   P   E   M   N   L   P   T   V   S   A   L 335          344          353          362          371          380
   AGG AAG ATG GGT GTG AAC CTG ACA CGC AGC AAC AAG GAG ACG GTG AAG CAC AGC
    R   K   M   G   V   N   L   T   R   S   N   K   E   T   V   K   H   S 389          398          407          416          425          434
   GAC GTC CTG TTT CTG GCT GTG AAG CCA CAT ATC ATC CCC TTC ATC CTG GAT GAG
    D   V   L   F   L   A   V   K   P   H   I   I   P   F   I   L   D   E

FIGURE 1A
```

```
     443              452              461          470              479              488
ATT GGG GCC GAC GTG CAA GCC AGA CAC ATC GTG GTC TCC TGT GCG GCT GGT GTC
 I   G   A   D   V   Q   A   R   H   I   V   V   S   C   A   A   G   V 497              506              515          524              533              542
ACC ATC AGC TCT GTG GAG AAG AAG CTG ATG GCA TTC CAG CCA GCC CCC AAA GTG
 T   I   S   S   V   E   K   K   L   M   A   F   Q   P   A   P   K   V 551              560              569          578              587              596
ATT CGC TGC ATG ACC AAC ACA CCT GTG GTA GTG CAG GAA GGC GCT ACA GTG TAC
 I   R   C   M   T   N   T   P   V   V   V   Q   E   G   A   T   V   Y 605              614              623          632              641              650
GCC ACG GGC ACC CAT GCC CTG GTG GAG GAT GGG CAG CTC CTG GAG CAG CTC ATG
 A   T   G   T   H   A   L   V   E   D   G   Q   L   L   E   Q   L   M 659              668              677          686              695              704
AGC AGT GTG GGC TTC TGC TGT ACT GAG GTG GAA GAG GAC CTC ATC GAT GCC GTC ACG
 S   S   V   G   F   C   C   T   E   V   E   E   D   L   I   D   A   V   T 713              722              731          740              749              758
GGG CTC AGT GGC AGC GGG CCT GCC TAT GCA TTC ATG GCT CTG GAC GCA TTG GCT
 G   L   S   G   S   G   P   A   Y   A   F   M   A   L   D   A   L   A 767              776              785          794              803              812
GAT GGT GGG GTG AAG ATG GGT TTG CCA CGG CGC CTG GCA ATC CAA CTC GGG GCC
 D   G   G   V   K   M   G   L   P   R   R   L   A   I   Q   L   G   A
```

FIGURE 1B

```
      821              830              839              848              857              866
CAG GCT TTG CTG GGA GCT GCC AAG ATG CTG CTG GAC TCG GAG CAG CAT CCA TGC
 Q   A   L   L   G   A   A   K   M   L   L   D   S   E   Q   H   P   C 875              884              893              902              911              920
CAG CTT AAG GAC AAT GTC TGC TCC CCT GGG GGA GCC ACC ATC CAC GCC CTG CAC
 Q   L   K   D   N   V   C   S   P   G   G   A   T   I   H   A   L   H 929              938              947              956              965              974
TTT CTA GAG AGT GGG GGC TTC CGC TCT CTG CTC ATC AAT GCA GTT GAG GCC TCC
 F   L   E   S   G   G   F   R   S   L   L   I   N   A   V   E   A   S 983              992             1001             1010             1019             1028
TGT ATC CGA ACA CGA GAG CTA CAG TCC ATG GCC GAC CAA GAA AAG ATC TCC CCA
 C   I   R   T   R   E   L   Q   S   M   A   D   Q   E   K   I   S   P 1037             1046             1055             1064             1073             1082
GCT GCC CTT AAG AAG ACC CTC TTA GAC AGA GTG AAG CTG GAA TCC CCC ACA GTC
 A   A   L   K   K   T   L   L   D   R   V   K   L   E   S   P   T   V 1091             1100             1109             1118             1127             1136
TCC ACA CTG ACC CCC AGC TCC AGC CCA GGG AAG CTC CTC ACA AGA AGC CTG GCC CTG
 S   T   L   T   P   S   S   S   P   G   K   L   L   T   R   S   L   A   L 1145             1154             1163             1172             1181             1190
GGA GGC AAG AAG GAC TAA GGC AGC ATC TGT CCC CTC TGT GAT TCA GAG CCC TTA
 G   G   K   K   D   *
```

FIGURE 1C

```
          1199       1208       1217       1226       1235       1244
     GTT GAG AGC CCC TGC CGC CCC TGC CAC CCC CCT GCC CCG CTC CCA CCA TTG CCC 1253       1262       1271       1280       1289       1298
     CTC CTC AGC TGT GCA AGG AGA AAG CAT GCT TAG GAA GTT TTC AGG TCC TTG TGA 1307       1316       1325       1334       1343       1352
     TAA AAC CTC CTT AAA TCT GTT CAG ACC AAG CAA TGC GAG CTT CCT CTC CTG TCC 1361       1370       1379       1388       1397       1406
     CAT GTT GGA AGT TGC TCT GAA GGG GTG GTA GAT GCT GGA AGC CAG ACA CAA CCC 1415       1424       1433       1442       1451       1460
     TGC GTA CGC TGC TCA GTT GGT GGA GAC TGG GGC TGG GAC TGG AGT CAG CCC AGC 1469       1478       1487       1496       1505       1514
     TGG GAG GAG GGG CTG GGG AGG ATC TGC AGC TGA AGC CCG AGG CAG GGT TGG TGT 1523       1532       1541       1550       1559       1568
     GAG CAG AAG GCA AAG TGG TGA GGA GAA AAC AGG AAA CGG GCT TTC TCT GAA TTG 1577       1586       1595       1604       1613       1622
     GAT GCC AAG GGG AAA GAA GTG AGC AAC TTA AGA TTG TCA CAA TTA ATC ACA AGT GTA 1631       1640       1649       1658       1667       1676
     GTA AAT GGG TTT ATA TTT AAC TCT TGC TTC ATA GGT GTA CCA TTT AAA 1631       1640       1649       1658       1667       1676
     CAG GAT TAG ACT GGG TTT ATA TTT AAC TCT TGC TTC ATA GGT GTA CCA TTT AAA
```

FIGURE 1D

```
      1685         1694         1703         1712         1721         1730
GAG TGT TAT TTA ATG CTA AGT TTA ACT GCT TTA ATA AAG TTT ATT TTT AAA TAT

1739
CAA AAA AAA AAA  3'
```

FIGURE 1E

```
      1 MSVGFIGAGQLAYALARGFTAAGILSAHKIIASSP    2278458
      1 MSVGFIGAGQLAFALAKGFTAAGVLAAHKIMASSP    g189498

36 EMNLPTVSALRKMGVNLTRSNKETVKHSDVLFLAV    2278458
     36 DMDLATVSALRKMGVKLTPHNKETVQHSDVLFLAV    g189498

71 KPHIIPFILDEIGADVQARHIVVSCAAGVTISSVE    2278458
     71 KPHIIPFILDEIGADIEDRHIVVSCAAGVTISSIE    g189498

106 KKLMAFQPAPKVIRCMTNTPVVVQEGATVYATGTH    2278458
    106 KKLSAFRPAPRVIRCMTNTPVVVREGATVYATGTH    g189498

141 ALVEDGQLLEQLMSSVGFCTEVEEDLIDAVTGLSG    2278458
    141 AQVEDGRLMEQLLSTVGFCTEVEEDLIDAVTGLSG    g189498

176 SGPAYAFMALDALADGGVKMGLPRRLAIQLGAQAL    2278458
    176 SGPAYAFTALDALADGGVKMGLPRRLAVRLGAQAL    g189498

211 LGAAKMLLDSEQHPCQLKDNVCSPGGATIHALHFL    2278458
    211 LGAAKMLLHSEQHPGQLKDNVSSPGGATIHALHVL    g189498
```

FIGURE 2A

246 ESGGFRSLLINAVEASCIRTRELQSMADQEKISPA 2278458
246 ESGGFRSLLINAVEASCIRTRELQSMADQEQVSPA g189498

281 ALKKTLLDRVKLESPTVSTLTPSSPGKLLTRSLAL 2278458
281 AIKKTILDKVKLDSPAGTALSPSGHTKLLPRSLAP g189498

316 GGKKD 2278458
316 AGK-D g189498

FIGURE 2B

DELTA 1-PYRROLINE-5-CARBOXYLATE REDUCTASE HOMOLOG

FIELD OF THE INVENTION

This invention relates to nucleic acid and amino acid sequences of a delta 1-pyrroline-5-carboxylate reductase homolog and to the use of these sequences in the diagnosis, treatment, and prevention of neuronal disorders, connective tissue disorders, and disorders of cell proliferation.

BACKGROUND OF THE INVENTION

Many pathways of biogenesis and biodegradation require oxidoreductase (dehydrogenase or reductase) activity, coupled to reduction or oxidation of a cofactor, such as $NAD(P)^+/NAD(P)H$. (Newsholme, E. A. and Leech, A. R. (1983) *Biochemistry for the Medical Sciences*, John Wiley and Sons, Chichester, U.K. pp. 779–793.) Reductase activity catalyzes the transfer of electrons with the oxidation of NADH and NADPH. The reverse dehydrogenase reaction reduces $NAD^+$ and $NADP^+$.

Delta 1-pyrroline-5-carboxylate reductase (P5CR) catalyzes the NAD(P) dependent oxidation of 1-pyrroline-5-carboxylate to proline, the terminal step in the biosynthesis of proline from glutamate. Proline is a critical substrate for the synthesis of collagen in tissues such as bone and interstitial fluid. In chondrocytes, P5CR is active during bone formation, and has a peak in activity which correlates with maximal collagen synthesis. P5CR may be involved in the regulation of nucleotide metabolism mediated by interaction with enzymes in the production of ribose phosphate. (Yeh et al. (1984) J. Biol. Chem. 259:5454–5458.) The enzyme activity is regulated by non-dietary controls. (Samuels et al. (1989) J. Nutr. 119:1900–1906.)

Proline is involved in a variety of disorders, including fibrosis. Cardiac fibrosis occurs, after myocardial infarction, in non-infarcted ventricular tissue and is associated with abnormal cardiac function. In hypertensive heart disease, reactive myocardial fibrosis is observed as an excessive accumulation of fibrillar collagen within the normal connective tissue of the myocardium. This accumulation increases in the presence of aldosterone, deoxycortisone, or angiotensin II. Collagen synthesis of cardiac fibroblasts decreases in the presence of prostaglandin E2. (Funck et al. (1997) Adv. Exp. Med. Biol. 432:35–44.) Proline levels are also increased in liver undergoing fibrosis due to chronic liver damage. Abnormalities of liver regeneration can contribute to chronic hepatitis, cirrhosis, and/or liver cancer. (Leevy, C. B. (1998) 16:88–98.) Lung hydroxyproline is an index of fibrosis in interstitial lung fibrosis. Leiomyomas are characterized by increased cell proliferation and tissue fibrosis. (Lee (1998) J. Clin. Endocrinol. Metab. 83:219–223.) Fibrosis in heart, liver, and lung, may be modified by inhibiting metabolites that regulate collagen deposition.

Some cancerous growth may involve increased or decreased P5CR activity. Treatments for chronic liver disease that inhibit the collagen-producing stellate cells have been reported to inhibit the development of hepatocellular carcinoma. (Sakaida et al. (1998) J. Hepatol. 28:298–306.) Deficiency of P5CR in a human leukemic lymphoblastoid cell line relative to normal human lymphocytes has been observed. (Lorans et al. (1978) Cancer Res. 38:3950–3953.) Raised P5CR activity distinguishes neoplastic from non-neoplastic colon cells. (Herzfeld et al. (1980) Cancer 46:2047–2054.)

Proline appears to modulate synaptic transmission in the mammalian brain. A subset of glutamate pathways involve high affinity proline transport and may be implicated in the seizures and mental retardation associated with genetic disorders of proline metabolism. Disorders of proline metabolism resulting in hyperprolinemia have been observed, at least one of which is associated with neuropsychiatric disorders that may be due to proline potentiation of transmission in cells of the hippocampus. (Cohen et al. (1997) Brain Res. 769:333–339; Cohen et al. (1997) Brain Res. 761:271–282.) Deficiency of another key enzyme in proline metabolism, prolidase, is associated with skin lesions, recurrent infections, mental retardation, and splenomegaly. P5CR deficiency has been observed in retinal degeneration. (Matsuzawa et al. (1982) Adv. Exp. Med. Biol. 153:361–370.)

The sequences of P5CR from eubacteria, archaeobacteria and eukaryotes show only a moderate level of overall similarity. P5CR is characterized by a conserved motif. (Delauney et al. (1990) Mol. Gen. Genet. 221:299–305).

The discovery of a new delta 1-pyrroline-5-carboxylate reductase homolog and the polynucleotides encoding it satisfies a need in the art by providing new compositions which are useful in the diagnosis, treatment, and prevention of neuronal disorders, connective tissue disorders and disorders of cell proliferation.

SUMMARY OF THE INVENTION

The invention is based on the discovery of a new human delta 1-pyrroline-5-carboxylate reductase homolog (P5CRH), the polynucleotides encoding P5CRH, and the use of these compositions for the diagnosis, treatment, or prevention of neuronal disorders, connective tissue disorders, and disorders of cell proliferation.

The invention features a substantially purified polypeptide comprising the amino acid sequence of SEQ ID NO:1 or a fragment of SEQ ID NO:1.

The invention further provides a substantially purified variant having at least 90% amino acid sequence identity to the amino acid sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 70% polynucleotide sequence identity to the polynucleotide encoding the polypeptide comprising the amino acid sequence of SEQ ID NO:1 or a fragment of SEQ ID NO:1.

The invention further provides an isolated and purified polynucleotide which hybridizes under stringent conditions to the polynucleotide encoding the polypeptide comprising the amino acid sequence of SEQ ID NO:1 or a fragment of SEQ ID NO:1, as well as an isolated and purified polynucleotide which is complementary to the polynucleotide encoding the polypeptide comprising the amino acid sequence of SEQ ID NO:1 or a fragment of SEQ ID NO:1.

The invention also provides an isolated and purified polynucleotide comprising the polynucleotide sequence of SEQ ID NO:2 or a fragment of SEQ ID NO:2, and an isolated and purified polynucleotide variant having at least 70% polynucleotide sequence identity to the polynucleotide comprising the polynucleotide sequence of SEQ ID NO:2 or a fragment of SEQ ID NO:2. The invention also provides an isolated and purified polynucleotide having a sequence complementary to the polynucleotide comprising the polynucleotide sequence of SEQ ID NO:2 or a fragment of SEQ ID NO:2.

The invention further provides an expression vector comprising at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising the amino acid sequence of SEQ ID NO:1 or a fragment of SEQ ID NO:1, the method comprising the steps of: (a) culturing the host cell comprising an expression vector containing at least a fragment of a polynucleotide encoding the polypeptide comprising the amino acid sequence of SEQ ID NO:1 or a fragment of SEQ ID NO:1 under conditions suitable for the expression of the polypeptide; and (b) recovering the polypeptide from the host cell culture.

The invention also provides a pharmaceutical composition comprising a substantially purified polypeptide having the sequence of SEQ ID NO:1 or a fragment of SEQ ID NO:1 in conjunction with a suitable pharmaceutical carrier.

The invention further includes a purified antibody which binds to a polypeptide comprising the sequence of SEQ ID NO:1 or a fragment of SEQ ID NO:1, as well as a purified agonist and a purified antagonist of the polypeptide.

The invention also provides a method for treating or preventing a neuronal disorder associated with decreased expression of activity of P5CRH, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a neuronal disorder associated with increased expression of activity of P5CRH, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing a connective tissue disorder associated with decreased expression of activity of P5CRH, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a connective tissue disorder associated with increased expression of activity of P5CRH, the method comprising administering to a subject in need of such treatment an effective amount of an antagonist of the polypeptide having the amino acid sequence of SEQ ID NO:1 or a fragment of SEQ ID NO:1.

The invention also provides a method for treating or preventing a disorder of cell proliferation associated with decreased expression of activity of P5CRH, the method comprising administering to a subject in need of such treatment an effective amount of a pharmaceutical composition comprising substantially purified polypeptide having the amino acid sequence of SEQ ID NO:1 or a fragment of SEQ ID NO:1.

The invention also provides a method for treating or preventing a disorder of cell proliferation associated with increased expression of activity of P5CRH, the method comprising administering to a subject in need of such treatment an effective amount of an antagonist of the polypeptide having the amino acid sequence of SEQ ID NO:1 or a fragment of SEQ ID NO:1.

The invention also provides a method for detecting a polynucleotide encoding a polypeptide comprising the amino acid sequence of SEQ ID NO:1 or a fragment of SEQ ID NO:1 in a biological sample containing nucleic acids, the method comprising the steps of: (a) hybridizing the complement of the polynucleotide encoding the polypeptide comprising the amino acid sequence of SEQ ID NO:1 or a fragment of SEQ ID NO:1 to at least one of the nucleic acids of the biological sample, thereby forming a hybridization complex; and (b) detecting the hybridization complex, wherein the presence of the hybridization complex correlates with the presence of a polynucleotide encoding the polypeptide comprising the amino acid sequence of SEQ ID NO:1 or a fragment of SEQ ID NO:1 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D and 1E show the amino acid sequence (SEQ ID NO:1) and nucleic acid sequence (SEQ ID NO:2) of P5CRH. The alignment was produced using MacDNASIS PRO™ software (Hitachi Software Engineering Co. Ltd., San Bruno, Calif.).

FIGS. 2A and 2B show the amino acid sequence alignments among P5CRH (2278458; SEQ ID NO:1), and pyrroline-5-carboxylate reductase (GI 189498; SEQ ID NO:3), produced using the multisequence alignment program of LASERGENE™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"P5CRH," as used herein, refers to the amino acid sequences of substantially purified P5CRH obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to P5CRH, increases or prolongs the duration of the effect of P5CRH. Agonists may include proteins, nucleic acids, carbohydrates, or any other molecules which bind to and modulate the effect of P5CRH.

An "allelic variant," as this term is used herein, is an alternative form of the gene encoding P5CRH. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding P5CRH, as described herein, include those sequences with deletions, insertions, or substitutions of different nucleotides, resulting in a polynucleotide the same as P5CRH or a polypeptide with at least one functional characteristic of P5CRH. Included within this definition are polymorphisms which may or may not be readily detectable using a particular oligonucleotide probe of the polynucleotide encoding P5CRH, and improper or unexpected hybridization to allelic variants, with a locus other than the normal chromosomal locus for the polynucleotide sequence encoding P5CRH. The encoded protein may also be "altered," and may contain deletions, insertions, or substitutions of amino acid residues which produce a silent change and result in a functionally equivalent P5CRH. Deliberate amino acid substitutions may be made on the basis of similarity in polarity, charge, solubility, hydrophobicity, hydrophilicity, and/or the amphipathic nature of the residues, as long as the biological or immunological activity of P5CRH is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of P5CRH which are preferably at least 5 to about 15 amino acids in length, most preferably at least 14 amino acids, and which retain some biological activity or immunological activity of P5CRH. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp. 1–5.)

The term "antagonist," as it is used herein, refers to a molecule which, when bound to P5CRH, decreases the amount or the duration of the effect of the biological or immunological activity of P5CRH. Antagonists may include proteins, nucleic acids, carbohydrates, antibodies, or any other molecules which decrease the effect of P5CRH.

As used herein, the term "antibody" refers to intact molecules as well as to fragments thereof, such as Fab, $F(ab')_2$, and Fv fragments, which are capable of binding the epitopic determinant. Antibodies that bind P5CRH polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic P5CRH, or of any oligopeptide thereof, to induce a specific immune response in appropriate animals or cells and to bind with specific antibodies.

The terms "complementary" or "complementarity," as used herein, refer to the natural binding of polynucleotides by base pairing. For example, the sequence "A—G—T" binds to the complementary sequence "T—C—A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation or an aqueous solution. Compositions comprising polynucleotide sequences encoding P5CRH or fragments of P5CRH may be employed as hybridization probes. The probes may be stored in freeze-dried form and may be associated with a stabilizing agent such as a carbohydrate. In hybridizations, the probe may be deployed in an aqueous solution containing salts, e.g., NaCl, detergents, e.g.,sodium dodecyl sulfate (SDS), and other components, e.g., Denhardt's solution, dry milk, salmon sperm DNA, etc.

"Consensus sequence," as used herein, refers to a nucleic acid sequence which has been resequenced to resolve uncalled bases, extended using XL-PCR™ (Perkin Elmer, Norwalk, Conn.) in the 5' and/or the 3' direction, and resequenced, or which has been assembled from the overlapping sequences of more than one Incyte Clone using a computer program for fragment assembly, such as the GELVIEW™ Fragment Assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding P5CRH, by Northern analysis is indicative of the presence of nucleic acids encoding P5CRH in a sample, and thereby correlates with expression of the transcript from the polynucleotide encoding P5CRH.

A "deletion," as the term is used herein, refers to a change in the amino acid or nucleotide sequence that results in the absence of one or more amino acid residues or nucleotides.

The term "derivative," as used herein, refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity," as used herein, refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or Northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MegAlign™ program (DNASTAR, Inc., Madison, Wis.). The MegAlign™ program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray," as used herein, refers to an arrangement of distinct polynucleotides arrayed on a substrate, e.g., paper, nylon or any other type of membrane, filter, chip, glass slide, or any other suitable solid support.

The terms "element" or "array element" as used herein in a microarray context, refer to hybridizable polynucleotides arranged on the surface of a substrate.

The term "modulate," as it appears herein, refers to a change in the activity of P5CRH. For example, modulation may cause an increase or a decrease in protein activity, binding characteristics, or any other biological, functional, or immunological properties of P5CRH.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked," as used herein, refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimer," "primer," "oligomer," and "probe," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding P5CRH, or fragments thereof, or P5CRH itself, may comprise a bodily fluid; an extract from a cell, chromosome, organelle, or membrane isolated from a cell; a cell; genomic DNA, RNA, or cDNA, in solution or bound to a solid support; a tissue; a tissue print; etc.

As used herein, the terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of P5CRH polypeptides, as used herein, refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE™ software.

The term "variant," when used in the context of a polynucleotide sequence, may encompass a polynucleotide sequence related to P5CRH. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

THE INVENTION

The invention is based on the discovery of a new human delta 1-pyrroline-5-carboxylate reductase homolog (P5CRH), the polynucleotides encoding P5CRH, and the use of these compositions for the diagnosis, treatment, or prevention of neuronal disorders, connective tissue disorders, and disorders of cell proliferation.

Nucleic acids encoding the P5CRH of the present invention were first identified in Incyte Clone 2278458 from the prostate cDNA library (PROSNON01) using a computer search, e.g., BLAST, for amino acid sequence alignments. A consensus sequence, SEQ ID NO:2, was derived from the following overlapping and/or extended nucleic acid sequences: Incyte Clones 2278458CB1 (PROSNON01), 676369H1 (CRBLNOT01), 1737410F6 (COLNNOT22), 538342H1 (LNODNOT02), 1707635F6 (DUODNOT02), 1830039F6 (THP1AZT01), and 1988068R6 (LUNGAST01).

In one embodiment, the invention encompasses a polypeptide comprising the amino acid sequence of SEQ ID NO:1, as shown in FIGS. 1A, 1B, 1C, 1D, and 1E. P5CRH is 320 amino acids in length and has a potential amidation site at residue G316; a potential N-glycosylation site at residue N51; six potential casein kinase II phosphorylation sites at residues S33, S55, S102, T160, S270, and T285; a potential glycosaminoglycan attachment site at residue S174; two potential protein kinase C phosphorylation sites at residues S55 and T59, a potential signal peptide from M1 to A18; and the delta 1-pyrroline-5-carboxylate reductase signature motif from residue G212 to L242. As shown in FIGS. 2A and 2B, P5CRH has chemical and structural similarity to pyrroline-5-carboxylate reductase (GI 189498). In particular, P5CRH and pyrroline-5- carboxylate reductase share 84% identity, five of the potential casein kinase II phosphorylation sites, the glycosaminoglycan attachment site, the signal peptide, and the 1-pyrroline-5-carboxylate reductase signature motif. A region of unique sequence in P5CRH from about amino acid 304 to about amino acid 306 is encoded by a fragment of SEQ ID NO:2 from about nucleotide 1103 to about nucleotide 1111. Northern analysis shows the expression of this sequence in various libraries, of which at least 30% are found in reproductive, 14% in nervous, 45% in cancerous, 21% in immortalized or proliferating tissues, and 30% in tissues involved in trauma or inflammatory response.

The invention also encompasses P5CRH variants. A preferred P5CRH variant is one which has at least about 80%, more preferably at least about 90%, and most preferably at least about 95% amino acid sequence identity to the P5CRH amino acid sequence, and which contains at least one functional or structural characteristic of P5CRH.

The invention also encompasses polynucleotides which encode P5CRH. In a particular embodiment, the invention encompasses a polynucleotide sequence comprising the sequence of SEQ ID NO:2, which encodes a P5CRH.

The invention also encompasses a variant of a polynucleotide sequence encoding P5CRH. In particular, such a variant polynucleotide sequence will have at least about 70%, more preferably at least about 80%, and most preferably at least about 90% polynucleotide sequence identity to the polynucleotide sequence encoding P5CRH. A particular aspect of the invention encompasses a variant of SEQ ID NO:2 which has at least about 70%, more preferably at least about 80%, and most preferably at least about 90% polynucleotide sequence identity to SEQ ID NO:2. Any one of the polynucleotide variants described above can encode an amino acid sequence which contains at least one functional or structural characteristic of P5CRH.

It will be appreciated by those skilled in the art that as a result of the degeneracy of the genetic code, a multitude of polynucleotide sequences encoding P5CRH, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring P5CRH, and all such variations are to be considered as being specifically disclosed.

Although nucleotide sequences which encode P5CRH and its variants are preferably capable of hybridizing to the nucleotide sequence of the naturally occurring P5CRH under appropriately selected conditions of stringency, it may be advantageous to produce nucleotide sequences encoding P5CRH or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding P5CRH and its derivatives without altering the encoded amino acid sequences include the production of RNA transcripts having more desirable properties, such as a greater half-life, than transcripts produced from the naturally occurring sequence.

The invention also encompasses production of DNA sequences which encode P5CRH and P5CRH derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding P5CRH or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50 % formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE® (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE™ Amplification System (GIBCO BRL, Gaithersburg, Md.). Preferably, sequence preparation is automated with machines such as the Hamilton Micro Lab 2200 (Hamilton, Reno, Nev.), Peltier Thermal Cycler (PTC200; MJ Research, Watertown, Mass.) and the ABI Catalyst 800 (Perkin Elmer). Sequencing is then carried out using either ABI DNA sequencers 372 and 373 (Perkin Elmer) or capillary electrophoresis (Molecular Dynamics). The resulting sequences are analyzed using a variety of alogorithms which are well known in the art.

The nucleic acid sequences encoding P5CRH may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PromoterFinder™ libraries to walk genomic DNA (Clontech, Palo Alto, Calif.). This procedure avoids the need to screen libraries and is useful in finding intron/exon junctions. For all PCR-based methods, primers may be designed using commercially available software, such as OLIGO™ 4.06 Primer Analysis software (National Biosciences Inc., Plymouth, Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., Genotyper™ and Sequence Navigator™, Perkin Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode P5CRH may be cloned in recombinant DNA molecules that direct expression of P5CRH, or fragments or functional equivalents thereof, in appropriate host cells. Due to the inherent degeneracy of the genetic code, other DNA sequences which encode substantially the same or a functionally equivalent amino acid sequence may be produced and used to express P5CRH.

The nucleotide sequences of the present invention can be engineered using methods generally known in the art in order to alter P5CRH-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding P5CRH may be synthesized, in whole or in part, using chemical methods well known in the art. (See, e.g., Caruthers, M. H. et al. (1980) Nucl. Acids Symp. Ser. (7):215–223; and Horn, T. et al. (1980) Nucl. Acids Symp. Ser. (7):225–232) Alternatively, P5CRH itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A peptide synthesizer (Perkin Elmer). Additionally, the amino acid sequence of P5CRH, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) *Proteins, Structures and Molecular Properties,* W H Freeman and Co., New York, N.Y.)

In order to express a biologically active P5CRH, the nucleotide sequences encoding P5CRH or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3 ' untranslated regions in the vector and in polynucleotide sequences encoding P5CRH. Such elements may vary in their strength and specificity. Specific initiation signals may also be used to achieve more efficient translation of sequences encoding P5CRH. Such signals include the ATG initiation codon and adjacent sequences, e.g. the Kozak sequence. In cases where sequences encoding P5CRH and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding P5CRH and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual,* Cold Spring Harbor Press, Plainview, N.Y., ch. 4, 8, and 16–17; and Ausubel, F. M. et al. (1995, and periodic supplements) *Current Protocols in Molecular Biology,* John Wiley & Sons, New York, N.Y., ch. 9, 13, and 16.)

A variety of expression vector/host systems may be utilized to contain and express sequences encoding P5CRH. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding P5CRH. For example, routine cloning, subcloning, and propagation of polynucleotide sequences encoding P5CRH can be achieved using a multifunctional *E. coli* vector such as Bluescript® (Stratagene) or pSport1™ plasmid (GIBCO BRL). Ligation of sequences encoding P5CRH into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of P5CRH are needed, e.g. for the production of antibodies, vectors which direct high level expression of P5CRH may be used. For example, vectors containing the strong, inducible T5 or T7 bacteriophage promoter may be used.

Yeast expression systems may be used for production of P5CRH. A number of vectors containing constitutive or inducible promoters, such as alpha factor, alcohol oxidase, and PGH, may be used in the yeast *Saccharomyces cerevisiae* or *Pichia pastoris.* In addition, such vectors direct either the secretion or intracellular retention of expressed proteins and enable integration of foreign sequences into the host genome for stable propagation. (See, e.g., Ausubel, supra; and Grant et al. (1987) Methods Enzymol. 153:516–54; Scorer, C. A. et al. (1994) Bio/Technology 12:181–184.)

Plant systems may also be used for expression of P5CRH. Transcription of sequences encoding P5CRH may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., Hobbs, S. or Murry, L. E. in *McGraw Hill Yearbook of Science and Technology* (1992) McGraw Hill, New York, N.Y.; pp. 191–196.)

In mammalian cells, a number of viral-based expression systems may be utilized. In cases where an adenovirus is used as an expression vector, sequences encoding P5CRH may be ligated into an adenovirus transcription/translation complex consisting of the late promoter and tripartite leader sequence. Insertion in a non-essential E1 or E3 region of the viral genome may be used to obtain infective virus which expresses P5CRH in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes.

For long term production of recombinant proteins in mammalian systems, stable expression of P5CRH in cell lines is preferred. For example, sequences encoding P5CRH can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; and Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP) (Clontech, Palo Alto, Calif.), β glucuronidase and its substrate β-D-glucuronoside, or luciferase and its substrate luciferin may be used. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding P5CRH is inserted within a marker gene sequence, transformed cells containing sequences encoding P5CRH can be identified by the absence of marker gene function. Alternatively, a marker gene can be placed in tandem with a sequence encoding P5CRH under the control of a single promoter. Expression of the marker gene in response to induction or selection usually indicates expression of the tandem gene as well.

In general, host cells that contain the nucleic acid sequence encoding P5CRH and that express P5CRH may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of P5CRH using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on P5CRH is preferred, but a competitive binding assay may be employed. These and other assays are well known in the art. (See, e.g., Hampton, R. et al. (1990) Serological Methods, a Laboratory Manual, APS Press, St Paul, Minn., Section IV; Coligan, J. E. et al. (1997 and periodic supplements) Current Protocols in Immunology, Greene Pub. Associates and Wiley-Interscience, New York, N.Y.; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding P5CRH include oligolabeling, nick translation, end-labeling, or PCR amplification using a labeled nucleotide. Alternatively, the sequences encoding P5CRH, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding P5CRH may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode P5CRH may be designed to contain signal sequences which direct secretion of P5CRH through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

In another embodiment of the invention, natural, modified, or recombinant nucleic acid sequences encoding P5CRH may be ligated to a heterologous sequence resulting in translation of a fusion protein in any of the aforementioned host systems. For example, a chimeric P5CRH protein containing a heterologous moiety that can be recognized by a commercially available antibody may facilitate the screening of peptide libraries for inhibitors of P5CRH activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA)

enable immunoaffinity purification of fusion proteins using commercially available monoclonal and polyclonal antibodies that specifically recognize these epitope tags. A fusion protein may also be engineered to contain a proteolytic cleavage site located between the P5CRH encoding sequence and the heterologous protein sequence, so that P5CRH may be cleaved away from the heterologous moiety following purification. Methods for fusion protein expression and purification are discussed in Ausubel, F. M. et al. (1995 and periodic supplements) *Current Protocols in Molecular Biology*, John Wiley & Sons, New York, N.Y., ch 10. A variety of commercially available kits may also be used to facilitate expression and purification of fusion proteins.

In a further embodiment of the invention, synthesis of radiolabeled P5CRH may be achieved in vitro using the TNT™ rabbit reticulocyte lysate or wheat germ extract systems (Promega, Madison, Wis.). These systems couple transcription and translation of protein-coding sequences operably associated with the T7, T3, or SP6 promoters. Translation takes place in the presence of a radiolabeled amino acid precursor, preferably $^{35}$S-methionine.

Fragments of P5CRH may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the Applied Biosystems 431A peptide synthesizer (Perkin Elmer). Various fragments of P5CRH may be synthesized separately and then combined to produce the full length molecule.

THERAPEUTICS

Chemical and structural similarity, in the context of sequences and motifs, exists between P5CRH and human delta 1-pyrroline-5-carboxylate reductase (GI 189498). In addition, P5CRH is expressed in reproductive, nervous, cancerous, immortalized, or proliferating tissues, and tissue involved in trauma or inflammatory response. Therefore, P5CRH appears to play a role in neuronal disorders, connective tissue disorders, and disorders of cell proliferation. In a disorder associated with increased expression of P5CRH, it is beneficial to decrease the expression of P5CRH. In a disorder associated with decreased expression of P5CRH, it is beneficial to provide the protein or increase the expression of P5CRH.

Therefore, in one embodiment, P5CRH or a fragment or derivative thereof may be administered to a subject to treat or prevent a neuronal disorder in which expression of P5CR is decreased. Such a neuronal disorder can include, but is not limited to, akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder.

In another embodiment, a vector capable of expressing P5CRH or a fragment or derivative thereof may be administered to a subject to treat or prevent a neuronal disorder including, but not limited to, those described above.

In a further embodiment, a pharmaceutical composition comprising a substantially purified P5CRH in conjunction with a suitable pharmaceutical carrier may be administered to a subject to treat or prevent a neuronal disorder including, but not limited to, those provided above.

In still another embodiment, an agonist which modulates the activity of P5CRH may be administered to a subject to treat or prevent a neuronal disorder including, but not limited to, those listed above.

In still another embodiment, an antagonist of P5CRH may be administered to a subject to treat or prevent a neuronal disorder in which expression of P5CR is increased. Such a neuronal disorder may include, but is not limited to, those listed above. In one aspect, an antibody which specifically binds P5CRH may be used directly as an antagonist or indirectly as a targeting or delivery mechanism for bringing a pharmaceutical agent to cells or tissue which express P5CRH.

In an additional embodiment, a vector expressing the complement of the polynucleotide encoding P5CRH may be administered to a subject to treat or prevent a neuronal disorder including, but not limited to, those listed above.

In one embodiment, P5CRH or a fragment or derivative thereof may be administered to a subject to treat or prevent a connective tissue disorder in which expression of P5CR is decreased. Such a connective tissue disorder can include, but is not limited to, cystic fibrosis, myocardial fibrosis, myelofibrosis, hepatic fibrosis, interstitial lung fibrosis, neoplastic fibrosis, pancreatic fibrosis, pulmonary fibrosis, subepidermal fibrosis, panmural fibrosis of the bladder, proliferative fibrosis, replacement fibrosis, retroperitoneal fibrosis and root sleeve fibrosis, osteogenesis imperfecta, Ehlers-Danlos syndrome, chondrodysplasias, Marfan syndrome, Alport syndrome, familial aortic aneurysm, achondroplasia, mucopolysaccharidoses, osteoporosis, osteopetrosis, Paget's disease, rickets, osteomalacia, hyperparathyroidism, renal osteodystrophy, osteonecrosis, osteomyelitis, osteoma, osteoid osteoma, osteoblastoma, osteosarcoma, osteochondroma, chondroma, chondroblastoma, chondromyxoid fibroma, chondrosarcoma, fibrous cortical defect, nonossifying fibroma, fibrous dysplasia, fibrosarcoma, malignant fibrous histiocytoma, Ewing's sarcoma, primitive neuroectodermal tumor, giant cell tumor, osteoarthritis, rheumatoid arthritis, ankylosing spondyloarthritis, Reiter's syndrome, psoriatic arthritis, enteropathic arthritis, infectious arthritis, gout, gouty arthritis, calcium pyrophosphate crystal deposition disease, ganglion, synovial cyst, villonodular synovitis, systemic sclerosis, Dupuytren's contracture, lupus erythematosus, mixed connective tissue disease, epidermolysis bullosa simplex, bullous congenital ichthyosiform erythroderma (epidermolytic hyperkeratosis), non-epidermolytic and epidermolytic palmoplantar keratodenna, ichthyosis bullosa of Siemens, pachyonychia congenita, and white sponge nevus.

In another embodiment, a vector capable of expressing P5CRH or a fragment or derivative thereof may be administered to a subject to treat or prevent a connective tissue disorder including, but not limited to, those described above.

In a further embodiment, a pharmaceutical composition comprising a substantially purified P5CRH in conjunction with a suitable pharmaceutical carrier may be administered to a subject to treat or prevent a connective tissue disorder including, but not limited to, those provided above.

In still another embodiment, an agonist which modulates the activity of P5CRH may be administered to a subject to treat or prevent a connective tissue disorder including, but not limited to, those listed above.

In a further embodiment, an antagonist of P5CRH may be administered to a subject to treat or prevent a connective tissue disorder in which expression of P5CR is increased. Such a connective tissue disorder may include, but is not limited to, those discussed above. In one aspect, an antibody which specifically binds P5CRH may be used directly as an antagonist or indirectly as a targeting or delivery mechanism for bringing a pharmaceutical agent to cells or tissue which express P5CRH.

In an additional embodiment, a vector expressing the complement of the polynucleotide encoding P5CRH may be administered to a subject to treat or prevent a connective tissue disorder including, but not limited to, those described above.

In one embodiment, P5CRH or a fragment or derivative thereof may be administered to a subject to treat or prevent a disorder of cell proliferation in which expression of P5CR is decreased. Such a disorder of cell proliferation can include, but is not limited to, actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing P5CRH or a fragment or derivative thereof may be administered to a subject to treat or prevent a disorder of cell proliferation including, but not limited to, those described above.

In a further embodiment, a pharmaceutical composition comprising a substantially purified P5CRH in conjunction with a suitable pharmaceutical carrier may be administered to a subject to treat or prevent a disorder of cell proliferation including, but not limited to, those provided above.

In still another embodiment, an agonist which modulates the activity of P5CRH may be administered to a subject to treat or prevent a disorder of cell proliferation including, but not limited to, those listed above.

In a further embodiment, an antagonist of P5CRH may be administered to a subject to treat or prevent a disorder of cell proliferation in which expression of P5CR is increased. Such a disorder of cell proliferation may include, but is not limited to, those discussed above. In one aspect, an antibody which specifically binds P5CRH may be used directly as an antagonist or indirectly as a targeting or delivery mechanism for bringing a pharmaceutical agent to cells or tissue which express P5CRH.

In an additional embodiment, a vector expressing the complement of the polynucleotide encoding P5CRH may be administered to a subject to treat or prevent a disorder of cell proliferation including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of P5CRH may be produced using methods which are generally known in the art. In particular, purified P5CRH may be used to produce antibodies or to screen libraries of pharmaceutical agents to identify those which specifically bind P5CRH. Antibodies to P5CRH may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with P5CRH or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to P5CRH have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of P5CRH amino acids may be fused with those of another protein, such as KLH, and antibodies to the chimeric molecule may be produced.

Monoclonal antibodies to P5CRH may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce P5CRH-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for P5CRH may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between P5CRH and its specific antibody. A two-site, monoclonal-based immunoassay utilizing monoclonal antibodies reactive to two non-interfering P5CRH epitopes is preferred, but a competitive binding assay may also be employed. (Maddox, supra.)

In another embodiment of the invention, the polynucleotides encoding P5CRH, or any fragment or complement thereof, may be used for therapeutic purposes. In one aspect, the complement of the polynucleotide encoding P5CRH may be used in situations in which it would be desirable to block the transcription of the mRNA. In particular, cells may be transformed with sequences complementary to polynucleotides encoding P5CRH. Thus, complementary molecules or fragments may be used to modulate P5CRH activity, or to achieve regulation of gene function. Such technology is now well known in the art, and sense or antisense oligonucleotides or larger fragments can be designed from various locations along the coding or control regions of sequences encoding P5CRH.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding P5CRH. (See, e.g., Sambrook, supra; and Ausubel, supra.)

Genes encoding P5CRH can be turned off by transforming a cell or tissue with expression vectors which express high levels of a polynucleotide, or fragment thereof, encoding P5CRH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding P5CRH. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches,* Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding P5CRH.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding P5CRH. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of P5CRH, antibodies to P5CRH, and mimetics, agonists, antagonists, or inhibitors of P5CRH. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of P5CRH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example P5CRH or fragments thereof, antibodies of P5CRH, and agonists, antagonists or inhibitors of P5CRH, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind P5CRH may be used for the diagnosis of disorders characterized by expression of P5CRH, or in assays to monitor patients being treated with P5CRH or agonists, antagonists, or inhibitors of P5CRH. Antibodies useful for diagnostic purposes may be prepared in the same manner as described above for therapeutics. Diagnostic assays for P5CRH include methods which utilize the antibody and a label to detect P5CRH in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring P5CRH, including ELISAs, RIAs, and FACS, are known in the art and provide a basis for diagnosing altered or abnormal levels of P5CRH expression. Normal or standard values for P5CRH expression are established by combining body fluids or cell extracts taken from normal mammalian subjects, preferably human, with antibody to P5CRH under conditions suitable for complex formation. The amount of standard complex formation may be quantitated by various methods, preferably by photometric means. Quantities of P5CRH expressed in subject samples, control and disease, from biopsied tissues are compared with the standard values. Deviation between standard and subject values establishes the parameters for diagnosing disease.

In another embodiment of the invention, the polynucleotides encoding P5CRH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of P5CRH may be correlated with disease. The diagnostic assay may be used to determine absence, presence, and excess expression of P5CRH, and to monitor regulation of P5CRH levels during therapeutic intervention.

In one aspect, hybridization with PCR probes which are capable of detecting polynucleotide sequences, including genomic sequences, encoding P5CRH or closely related molecules may be used to identify nucleic acid sequences which encode P5CRH. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding P5CRH, allelic variants, or related sequences.

Probes may also be used for the detection of related sequences, and should preferably have at least 50% sequence identity to any of the P5CRH encoding sequences. The hybridization probes of the subject invention may be DNA or RNA and may be derived from the sequence of SEQ ID NO:2 or from genomic sequences including promoters, enhancers, and introns of the P5CRH gene.

Means for producing specific hybridization probes for DNAs encoding P5CRH include the cloning of polynucleotide sequences encoding P5CRH or P5CRH derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding P5CRH may be used for the diagnosis of a disorder associated with expression of P5CRH. Examples of such a disorder include, but are not limited to, neuronal disorders such as akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, peripheral neuropathy, multiple sclerosis, neurofibromatosis, Parkinson's disease, paranoid psychoses, postherpetic neuralgia, schizophrenia, and Tourette's disorder; connective tissue disorders such as cystic fibrosis, myocardial fibrosis, myelofibrosis, hepatic fibrosis, interstitial lung fibrosis, neoplastic fibrosis, pancreatic fibrosis, pulmonary fibrosis, subepidermal fibrosis, panmural fibrosis of the bladder, proliferative fibrosis, replacement fibrosis, retroperitoneal fibrosis and root sleeve fibrosis, osteogenesis imperfecta, Ehlers-Danlos syndrome, chondrodysplasias, Marfan syndrome, Alport syndrome, familial aortic aneurysm, achondroplasia, mucopolysaccharidoses, osteoporosis, osteopetrosis, Paget's disease, rickets, osteomalacia, hyperparathyroidism, renal osteodystrophy, osteonecrosis, osteomyelitis, osteoma, osteoid osteoma, osteoblastoma, osteosarcoma, osteochondroma, chondroma, chondroblastoma, chondromyxoid fibroma, chondrosarcoma, fibrous cortical defect, nonossifying fibroma, fibrous dysplasia, fibrosarcoma, malignant fibrous histiocytoma, Ewing's sarcoma, primitive neuroectodermal tumor, giant cell tumor, osteoarthritis, rheumatoid arthritis, ankylosing spondyloarthritis, Reiter's syndrome, psoriatic arthritis, enteropathic arthritis, infectious arthritis, gout, gouty arthritis, calcium pyrophosphate crystal deposition disease, ganglion, synovial cyst, villonodular synovitis, systemic sclerosis, Dupuytren's contracture, lupus erythematosus, mixed connective tissue disease, epidermolysis bullosa simplex, bullous congenital ichthyosiform erythroderma (epidermolytic hyperkeratosis), non-epidermolytic and epidermolytic palmoplantar keratoderma, ichthyosis bullosa of Siemens, pachyonychia congenita, and white sponge nevus; and disorders of cell proliferation such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding P5CRH may be used in Southern or Northern analysis, dot blot, or other membrane-based technologies; in PCR technologies; in dipstick, pin, and ELISA assays; and in microarrays utilizing fluids or tissues from patients to detect altered P5CRH expression. Such qualitative or quantitative methods are well known in the art.

In a particular aspect, the nucleotide sequences encoding P5CRH may be useful in assays that detect the presence of associated disorders, particularly those mentioned above. The nucleotide sequences encoding P5CRH may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding P5CRH in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of P5CRH, a normal or standard profile for expression is established. This may be accomplished by combining body fluids or cell extracts taken from normal subjects, either animal or human, with a sequence, or a fragment thereof, encoding P5CRH, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding P5CRH may involve the use of PCR. These oligomers may be chemically synthesized, generated enzymatically, or produced in vitro. Oligomers will preferably contain a fragment of a polynucleotide encoding P5CRH, or a fragment of a polynucleotide complementary to the polynucleotide encoding P5CRH, and will be employed under optimized conditions for identification of a specific gene or condition. Oligomers may also be employed under less stringent conditions for detection or quantitation of closely related DNA or RNA sequences.

Methods which may also be used to quantitate the expression of P5CRH include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding P5CRH may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology,* VCH Publishers New York, N.Y., pp. 965–968.) Examples of genetic map data can be found in various scientific journals or at the Online Mendelian Inheritance in Man (OMIM) site. Correlation between the location of the gene encoding P5CRH on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, P5CRH, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between P5CRH and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with P5CRH, or fragments thereof, and washed. Bound P5CRH is then detected by methods well known in the art. Purified P5CRH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding P5CRH specifically compete with a test compound for binding P5CRH. In this manner, antibodies can be used to detect the presence of any peptide which shares one or more antigenic determinants with P5CRH.

In additional embodiments, the nucleotide sequences which encode P5CRH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. PROSNON01 cDNA Library Construction

The PROSNON01 normalized cDNA library was constructed from microscopically normal prostate tissue obtained from a 28-year-old Caucasian male who died from a self inflicted gun shot wound.

The frozen tissue was homogenized and lysed using a Brinkmann Homogenizer Polytron PT-3000 (Brinkmann Instruments, Westbury, N.Y.) in guanidinium isothiocyanate solution. The lysate was centrifuged over a 5.7 M CsCl cushion using an SW28 rotor in a Beckman L8-70M ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and treated with DNase at 37° C. RNA was extracted and precipitated as before. The mRNA was then isolated using the Qiagen Oligotex kit (QIAGEN, Inc., Chatsworth, Calif.) and used to construct the cDNA library.

The RNA was handled according to the recommended protocols in the SuperScript plasmid system(Catalog #18248-013; Life Technologies). cDNA synthesis was initiated with a NotI-oligo d(T) primer. The cDNAs were fractionated on a Sepharose CL4B column (Catalog #275105-01, Pharmacia), and those cDNAs exceeding 400 bp were ligated into the NotI and SolI sites of pSport 1. The plasmid pSport 1 was subsequently transformed into DH5α™ competent cells (Catalog #18258-012, Life Technologies).

II. Normalization, Isolation and Sequencing of cDNA Clones $4.4 \times 10^6$ independent clones of the PROSNON01 plasmid library in E. Coli strain DH12S (catalog #18312-0127, Life Technologies) were grown in liquid culture under carbenicillin (25 mg/l) and methicillin (1 mg/ml) selection following transformation by electorporation. The culture was checked spectrophotometrically (Model DU-7 Spectrophotometer, Beckman Instruments) and allowed to grow to an OD600 of 0.2 and then superinfected with a 5-fold excess of the helper phage M13K07 according to the method of Vieira et al. (1987, Methods Enzymol. 153:3–11).

To reduce the number of excess cDNA copies according to their abundance levels in the library, the cDNA library was then normalized in a single round according to the procedure of Soares et al. (1994, Proc. Natl. Acad. Sci. 91:9928–9932) with the following modifications. The primer to template ratio in the primer extension reaction was increased from 2:1 to 10:1. The ddNTP concentration in this reaction was reduced to 150 $\mu$M each ddNTP, allowing the generation of longer (400–1000 nt) primer extension products. The reannealing hybridization was extended from 13 to 19 hours. The single stranded DNA circles of the normalized library were purified by hydroxyapatite chromatography and converted to partially double-stranded by random priming, followed by electroporation into DH10B™ competent bacteria (Life Technologies).

Plasmid DNA was released from the cells and purified using the REAL Prep 96 plasmid kit (Catalog #26173, QIAGEN, Inc.). The recommended protocol was employed except for the following changes: 1) the bacteria were cultured in 1 ml of sterile Terrific Broth (Catalog #22711, Life Technologies) with carbenicillin at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems; and the reading frame was determined.

III. Similarity Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of similarity using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-8}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for similarity.

Additionally, sequences identified from cDNA libraries may be analyzed to identify those gene sequences encoding conserved protein motifs using an appropriate analysis program, e.g., BLOCKS. BLOCKS is a weighted matrix analysis algorithm based on short amino acid segments, or blocks, compiled from the PROSITE database. (Bairoch, A. et al. (1997) Nucleic Acids Res. 25:217–221.) The BLOCKS algorithm is useful for classifying genes with unknown functions. (Henikoff, S. and Henikoff, G. J., Nucleic Acids Research (1991) 19:6565–6572.) Blocks, which are 3 to 60 amino acids in length, correspond to the most highly conserved regions of proteins. The BLOCKS algorithm compares a query sequence with a weighted scoring matrix of blocks in the BLOCKS database. Blocks in the BLOCKS database are calibrated against protein sequences with known functions from the SWISS-PROT database to determine the stochastic distribution of matches. Similar databases such as PRINTS, a protein fingerprint database, are also searchable using the BLOCKS algorithm. (Attwood, T. K. et al. (1997) J. Chem. Inf. Comput. Sci. 37:417–424.) PRINTS is based on non-redundant sequences obtained from sources such as SWISS-PROT, GenBank, PIR, and NRL-3D.

The BLOCKS algorithm searches for matches between a query sequence and the BLOCKS or PRINTS database and evaluates the statistical significance of any matches found. Matches from a BLOCKS or PRINTS search can be evaluated on two levels, local similarity and global similarity. The degree of local similarity is measured by scores, and the extent of global similarity is measured by score ranking and probability values. A score of 1000 or greater for a BLOCKS match of highest ranking indicates that the match falls within the 0.5 percentile level of false positives when the matched block is calibrated against SWISS-PROT. Likewise, a probability value of less than $1.0 \times 10^{-3}$ indicates that the match would occur by chance no more than one time in every 1000 searches. Only those matches with a cutoff score of 1000 or greater and a cutoff probability value of $1.0 \times 10^{-3}$ or less are considered in the functional analyses of the protein sequences in the Sequence Listing.

Nucleic and amino acid sequences of the Sequence Listing may also be analyzed using PFAM. PFAM is a Hidden Markov Model (HMM) based protocol useful in protein family searching. HMM is a probabilistic approach which analyzes consensus primary structures of gene families. (See, e.g., Eddy, S. R. (1996) Cur. Opin. Str. Biol. 6:361–365.)

The PFAM database contains protein sequences of 527 protein families gathered from publicly available sources, e.g., SWISS-PROT and PROSITE. PFAM searches for well characterized protein domain families using two high-quality alignment routines, seed alignment and full alignment. (See, e.g., Sonnhammer, E. L. L. et al. (1997) Proteins 28:405–420.) The seed alignment utilizes the hmmls program, a program that searches for local matches, and a non-redundant set of the PFAM database. The full alignment utilizes the hmmfs program, a program that searches for multiple fragments in long sequences, e.g., repeats and motifs, and all sequences in the PFAM database. A result or score of 100 "bits" can signify that it is $2^{100}$-fold more likely that the sequence is a true match to the model or comparison sequence. Cutoff scores which range from 10 to 50 bits are generally used for individual protein families using the SWISS-PROT sequences as model or comparison sequences.

Two other algorithms, SIGPEPT and TM, both based on the HMM algorithm described above (see, e.g., Eddy, supra; and Sonnhammer, supra), identify potential signal sequences and transmembrane domains, respectively. SIGPEPT was created using protein sequences having signal sequence annotations derived from SWISS-PROT. It contains about 1413 non-redundant signal sequences ranging in length from 14 to 36 amino acid residues. TM was created similarly using transmembrane domain annotations. It contains about 453 non-redundant transmembrane sequences encompassing 1579 transmembrane domain segments. Suitable HMM models were constructed using the above sequences and were refined with known SWISS-PROT signal peptide sequences or transmembrane domain sequences until a high correlation coefficient, a measurement of the correctness of the analysis, was obtained. Using the protein sequences from the SWISS-PROT database as a test set, a cutoff score of 11 bits, as determined above, correlated with 91–94% true-positives and about 4.1% false-positives, yielding a correlation coefficient of about 0.87–0.90 for SIGPEPT. A score of 11 bits for TM will typically give the following results: 75% true positives; 1.72% false positives; and a correlation coefficient of 0.76. Each search evaluates the statistical significance of any matches found and reports only those matches that score at least 11 bits.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST were used to search for identical or related molecules in nucleotide databases such as GenBank or LIFESEQ™ database (Incyte Pharmaceuticals). This analysis is much faster than multiple membrane-based hybridizations. In addition, the sensitivity of the computer search can be modified to determine whether any particular match is categorized as exact or similar.

The basis of the search is the product score, which is defined as:

% sequence identity×% maximum BLAST score/100

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of Northern analysis are reported as a list of libraries in which the transcript encoding P5CRH occurs. Abundance and percent abundance are also reported. Abundance directly reflects the number of times a particular transcript is represented in a cDNA library, and percent abundance is abundance divided by the total number of sequences examined in the cDNA library.

V. Extension of P5CRH Encoding Polynucleotides

The nucleic acid sequence of Incyte Clone 2278458 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO™ 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR™ kit (Perkin Elmer) and thoroughly mixing the enzyme and reaction mix. PCR was performed using the Peltier Thermal Cycler (PTC200; M. J. Research, Watertown, Mass.), beginning with 40 pmol of each primer and the recommended concentrations of all other components of the kit, with the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK™ (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2×carb). The following day, several colonies were randomly picked from each plate and cultured in 150 µl of liquid LB/2×carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO™ 4.06 software (National Biosciences) and labeled by combining 50 pmol of each oligomer, 250 µCi of [γ-$^{32}$P] adenosine triphosphate (Amersham, Chicago, Ill.), and T4 polynucleotide kinase (DuPont NEN®, Boston, Mass.). The labeled oligonucleotides are substantially purified using a Sephadex™ G-25 superfine size exclusion dextran bead column (Pharmacia & Upjohn, Kalamazoo, Mich.). An aliquot containing $10^7$ counts per minute of the labeled probe is used in a typical membrane-based hybridization analysis of human genomic DNA digested with one of the following endonucleases: Ase I, Bgl II, Eco RI, Pst I, XbaI, or Pvu II (DuPont NEN, Boston, Mass.).

The DNA from each digest is fractionated on a 0.7% agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester, N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE™. Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467–470; and Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the P5CRH-encoding sequences, or any parts thereof, are used to detect, decrease, or inhibit expression of naturally occurring P5CRH. Although use of oligonucleotides comprising from about 15 to 30 base pairs is described, essentially the same procedure is used with smaller or with larger sequence fragments. Appropriate oligonucleotides are designed using OLIGO™ 4.06 software and the coding sequence of P5CRH. To inhibit transcription, a complementary oligonucleotide is designed from the most unique 5' sequence and used to prevent promoter binding to the coding sequence. To inhibit translation, a complementary oligonucleotide is designed to prevent ribosomal binding to the P5CRH-encoding transcript.

IX. Expression of P5CRH

Expression and purification of P5CRH is achieved using bacterial or virus-based expression systems. For expression of P5CRH in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express P5CRH upon induction with isopropyl beta-D-thiogalactopyranoside (IPTG). Expression of P5CRH in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding P5CRH by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, P5CRH is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Pharmacia, Piscataway, N.J.). Following purification, the GST moiety can be proteolytically cleaved from P5CRH at specifically engineered sites. FLAG, an 8-amino acid peptide, enables immunoaffinity purification using commercially available monoclonal and polyclonal anti-FLAG antibodies (Eastman Kodak, Rochester, N.Y.). 6-His, a stretch of six consecutive histidine residues, enables purification on metal-chelate resins (QIAGEN Inc, Chatsworth, Calif.). Methods for protein expression and purification are discussed in Ausubel, F. M. et al. (1995 and periodic supplements) *Current Protocols in Molecular Biology*, John Wiley & Sons, New York, N.Y., ch 10, 16. Purified P5CRH obtained by these methods can be used directly in the following activity assay.

X. Demonstration of P5CRH Activity

P5CRH activity is measured by the conversion of pyrroline-5-carboxylate to proline. 0.03 $\mu$Ci of [U-$^{14}$C] pyrroline-5-carboxylate, 0.25 $\mu$mol of pyrroline-5-carboxylate, 0.25 $\mu$mol of NADH, and 25 $\mu$mol of potassium phosphate buffer, pH t.8, are incubated with aliquots of enzyme preparations in a total volume of 0.25 ml. After a 10-min. incubation at 37° C., the reaction is terminated with the addition of 50 $\mu$l of orthoaminobenzaldehyde (30 mg/ml in 10% ethanol, 90% 6 N HCl). The mixture is boiled for 5 min. in a water bath and centrifuged at 2000 rpm for 10 min. A 200 $\mu$l aliquot of the supernatant is applied to a 1 ml bed volume column of Ag-50, 200–400 mesh (BioRad). Product proline is eluted with 1 N HCl, and radioactivity is determined by liquid scintillation counting. (Merrill et al. (1989) J. Biol. Chem. 264:9352–9358.)

XI. Functional Assays

P5CRH function is assessed by expressing the sequences encoding P5CRH at physiologically elevated levels in mammalian cell culture systems. cDNA is subcloned into a mammalian expression vector containing a strong promoter that drives high levels of cDNA expression. Vectors of choice include pCMV SPORT™ (Life Technologies, Gaithersburg, Md.) and pCR™ 3.1 (Invitrogen, Carlsbad, Calif., both of which contain the cytomegalovirus promoter. 5–10 $\mu$g of recombinant vector are transiently transfected into a human cell line, preferably of endothelial or hematopoietic origin, using either liposome formulations or electroporation. 1–2 $\mu$g of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP) (Clontech, Palo Alto, Calif.), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; downregulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York, N.Y.

The influence of P5CRH on gene expression can be assessed using highly purified populations of cells transfected with sequences encoding P5CRH and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success, N.Y.). mRNA can be purified from the cells using methods well known by those of skill in the art. Expression of mRNA encoding P5CRH and other genes of interest can be analyzed by Northern analysis or microarray techniques.

XII. Production of P5CRH Specific Antibodies

P5CRH substantially purified using polyacrylamide gel electrophoresis (PAGE) (see, e.g., Harrington, M. G. (1990) Methods Enzymol. 182:488–495), or other purification techniques, is used to immunize rabbits and to produce antibodies using standard protocols.

Alternatively, the P5CRH amino acid sequence is analyzed using LASERGENE™ software (DNASTAR Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel supra, ch. 11.)

Typically, oligopeptides 15 residues in length are synthesized using an Applied Biosystems Peptide Synthesizer Model 431A using fmoc-chemistry and coupled to KLH (Sigma, St. Louis, Mo.) by reaction with N-maleimidobenzoyl-N-hydroxysuccinimide ester (MBS) to increase immunogenicity. (See, e.g., Ausubel supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring P5CRH Using Specific Antibodies

Naturally occurring or recombinant P5CRH is substantially purified by immunoaffinity chromatography using antibodies specific for P5CRH. An immunoaffinity column is constructed by covalently coupling anti-P5CRH antibody to an activated chromatographic resin, such as CNBr-activated Sepharose (Pharmacia & Upjohn). After the coupling, the resin is blocked and washed according to the manufacturer's instructions.

Media containing P5CRH are passed over the immunoaffinity column, and the column is washed under conditions that allow the preferential absorbance of P5CRH (e.g., high ionic strength buffers in the presence of detergent). The column is eluted under conditions that disrupt antibody/P5CRH binding (e.g., a buffer of pH 2 to pH 3, or a high concentration of a chaotrope, such as urea or thiocyanate ion), and P5CRH is collected.

XIV. Identification of Molecules Which Interact with P5CRH

P5CRH, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled P5CRH, washed, and any wells with labeled P5CRH complex are assayed. Data obtained using different concentrations of P5CRH are used to calculate values for the number, affinity, and association of P5CRH with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide encoding a polypeptide selected from:

a) SEQ ID NO:1, b) a fragment of SEQ ID NO:1 from about amino acid residue R17 to about amino acid residue P40, and c) a fragment of SEQ ID NO:1 from about amino acid residue K276 to about amino acid residue T299.

2. An isolated and purified polynucleotide which hybridizes under high stringency wash conditions at room temperature in 0.1×saline sodium citrate and 0.5% sodium dodecyl sulfate to the polynucleotide of claim 1.

3. An isolated and purified polynucleotide which hybridizes under stringent conditions to the polynucleotide of claim 1.

4. An isolated and purified polynucleotide which is completely complementary to the polynucleotide of claim 1.

5. An isolated and purified polynucleotide comprising the polynucleotide sequence of SEQ ID NO:2 or a fragment of SEQ ID NO:2 of at least 60 contiguous nucleotides 5' of nucleotide 1350 of SEQ ID NO:2.

6. An isolated and purified polynucleotide variant having at least 70% polynucleotide sequence identity to the polynucleotide of claim 5.

7. An isolated and purified polynucleotide having a sequence completely complementary to the polynucleotide of claim 5.

8. An expression vector comprising the polynucleotide of claim 1.

9. A host cell comprising the expression vector of claim 8.

10. A method for producing a polypeptide, the method comprising the steps of:
   (a) culturing the host cell of claim 9 under conditions suitable for the expression of the polypeptide; and
   (b) recovering the polypeptide from the host cell culture.

11. A method for detecting a polynucleotide in a sample containing nucleic acids, the method comprising the steps of:

(a) hybridizing the polynucleotide of claim 4 to at least one of the nucleic acids of the sample, thereby forming a hybridization complex; and
   (b) detecting the hybridization complex, wherein the presence of the hybridization complex correlates with the presence of a polynucleotide encoding the polypeptide in the sample.

12. The method of claim 11 wherein the nucleic acids of the biological sample are amplified by the polymerase chain reaction prior to the hybridizing step.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 314 amino acids
      (B) TYPE: amino acid
      (C) STRANDEDNESS: single
      (D) TOPOLOGY: linear (vii) IMMEDIATE SOURCE:
              (A) LIBRARY: PROSNON01
              (B) CLONE: 2278458

(xi) SEQUENCE DESCRIPTION: SEQ ID NO:1:

```
Met Ser Val Gly Phe Ile Gly Ala Gly Gln Leu Ala Tyr Arg Phe Thr
 1               5                  10                  15

Ala Ala Gly Ile Leu Ser Ala His Lys Ile Ile Ala Ser Ser Pro Glu
                20                  25                  30

Met Asn Leu Pro Thr Val Ser Ala Leu Arg Lys Met Gly Val Asn Leu
            35                  40                  45

Thr Arg Ser Asn Lys Glu Thr Val Lys His Ser Asp Val Leu Phe Leu
 50                  55                  60

Ala Val Lys Pro His Ile Ile Pro Phe Ile Leu Asp Glu Ile Gly Ala
 65                  70                  75                  80

Asp Val Gln Ala Arg His Ile Val Val Ser Cys Ala Ala Gly Val Thr
                85                  90                  95

Ile Ser Ser Val Glu Lys Lys Leu Met Ala Phe Gln Pro Ala Pro Lys
                100                 105                 110

Val Ile Arg Cys Met Thr Asn Thr Pro Val Val Gln Glu Gly Ala
                115                 120                 125

Thr Val Tyr Ala Thr Gly Thr His Ala Leu Val Glu Asp Gly Gln Leu
130                 135                 140

Leu Glu Gln Leu Met Ser Ser Val Gly Phe Cys Thr Glu Val Glu Glu
145                 150                 155                 160

Asp Leu Ile Asp Ala Val Thr Gly Leu Ser Gly Ser Gly Pro Ala Tyr
                165                 170                 175

Ala Phe Met Ala Leu Asp Ala Asp Gly Gly Val Lys Met Gly Leu Pro
                180                 185                 190

Arg Arg Leu Ala Ile Gln Leu Gly Ala Gln Ala Leu Leu Gly Ala Ala
                195                 200                 205

Lys Met Leu Leu Asp Ser Glu Gln His Pro Cys Gln Leu Lys Asp Asn
210                 215                 220

Val Cys Ser Pro Gly Gly Ala Thr Ile His Ala Leu His Phe Leu Glu
225                 230                 235                 240

Ser Gly Gly Phe Arg Ser Leu Leu Ile Asn Ala Val Glu Ala Ser Cys
                245                 250                 255

Ile Arg Thr Arg Glu Leu Gln Ser Met Ala Asp Gln Glu Lys Ile Ser
                260                 265                 270

Pro Ala Ala Leu Lys Lys Thr Leu Leu Asp Arg Val Lys Leu Glu Ser
                275                 280                 285

Pro Thr Val Ser Thr Leu Thr Pro Ser Ser Pro Gly Lys Leu Leu Thr
                290                 295                 300

Arg Ser Leu Ala Leu Gly Gly Lys Lys Asp
305                 310
```

(2) INFORMATION FOR SEQ ID NO:2:

(i) SEQUENCE CHARACTERISTICS:
         (A) LENGTH: 1742 base pairs
         (B) TYPE: nucleic acid
         (C) STRANDEDNESS: single
         (D) TOPOLOGY: linear (vii) IMMEDIATE SOURCE:
          (A) LIBRARY: PROSNON01
          (B) CLONE: 2278458

(xi) SEQUENCE DESCRIPTION: SEQ ID NO:2:

```
GCGCCATCAG CCGCCCGGGA GATATCCGCC GGGGGAGAAT AGGGTTGCAC CATCCCAGAA     60
GCTGCTGTTA GCTCGCCGGT CCTCGGCACG CCGCCCGTTC GCCCCTGCGC TGTCCGCCCT    120
TCCCCTAGCG TTACTTCCGG TCCCTCGCTG AGGGGGTTCG TGCGGCTCCC AGGAGGCGTG    180
AACCGCGGAC CATGAGCGTG GGCTTCATCG GGGCCGGCCA GCTGGCCTAT GCTCTGGCGC    240
GGGGCTTCAC GGCCGCAGGC ATCCTGTCGG CTCACAAGAT AATAGCCAGC TCCCCAGAAA    300
TGAACCTGCC CACGGTGTCC GCGCTCAGGA AGATGGGTGT GAACCTGACA CGCAGCAACA    360
AGGAGACGGT GAAGCACAGC GACGTCCTGT TTCTGGCTGT GAAGCCACAT ATCATCCCCT    420
TCATCCTGGA TGAGATTGGG GCCGACGTGC AAGCCAGACA CATCGTGGTC TCCTGTGCGG    480
CTGGTGTCAC CATCAGCTCT GTGGAGAAGA AGCTGATGGC ATTCCAGCCA GCCCCCAAAG    540
TGATTCGCTG CATGACCAAC ACACCTGTGG TAGTGCAGGA AGGCGCTACA GTGTACGCCA    600
CGGGCACCCA TGCCCTGGTG GAGGATGGGC AGCTCCTGGA GCAGCTCATG AGCAGCGTGG    660
GCTTCTGCAC TGAGGTGGAA GAGGACCTCA TCGATGCCGT CACGGGGCTC AGTGGCAGCG    720
GGCCTGCCTA TGCATTCATG GCTCTGGACG CATTGGCTGA TGGTGGGGTG AAGATGGGTT    780
TGCCACGGCG CCTGGCAATC CAACTCGGGG CCCAGGCTTT GCTGGGAGCT GCCAAGATGC    840
TGCTGGACTC GGAGCAGCAT CCATGCCAGC TTAAGGACAA TGTCTGCTCC CCTGGGGGAG    900
CCACCATCCA CGCCCTGCAC TTTCTAGAGA GTGGGGCTT CCGCTCTCTG CTCATCAATG    960
CAGTTGAGGC CTCCTGTATC CGAACACGAG AGCTACAGTC CATGGCCGAC CAAGAAAAGA   1020
TCTCCCCAGC TGCCCTTAAG AAGACCCTCT TAGACAGAGT GAAGCTGGAA TCCCCCACAG   1080
TCTCCACACT GACCCCCTCC AGCCCAGGGA AGCTCCTCAC AAGAAGCCTG GCCCTGGGAG   1140
GCAAGAAGGA CTAAGGCAGC ATCTGTCCCC TCTGTGATTC AGAGCCCTTA GTTGAGAGCC   1200
CCTGCCGCCC CTGCCACCCC CCTGCCCCGC TCCCACCATT GCCCCTCCTC AGCTGTGCAA   1260
GGAGAAAGCA TGCTTAGGAA GTTTTCAGGT CCTTGTGATA AAACCTCCTT AAATCTGTTC   1320
AGACCAAGCA ATGCGAGCTT CCTCTCCTGT CCCATGTTGG AAGTTGCTCT GAAGGGGTGG   1380
TAGATGCTGG AAGCCAGACA CAACCCTGCG TACGCTGCTC AGTTGGTGGA GACTGGGGCT   1440
GGGACTGGAG TCAGCCCAGC TGGGAGGAGG GGCTGGGGAG GATCTGCAGC TGAAGCCCGA   1500
GGCAGGGTTG GTGTGATGCC AAGGCAAAGT GGTGAGGAGA AAACAGGAAA CGGGCTTTCT   1560
CTGAATTGGT AAATGGGAAA GAAGTGAGCA ACTTAAGATT GTCACAATTA ATCACAAGTG   1620
TACAGGATTA GACTGGGTTT ATATTTAACT CTTGCTTCAT AGGTGTACCA TTTAAAGAGT   1680
GTTATTTAAT GCTAAGTTTA ACTGCTTTAA TAAAGTTTAT TTTTAAATAT CAAAAAAAAA   1740
AA                                                                  1742
```

(2) INFORMATION FOR SEQ ID NO:3:

(i) SEQUENCE CHARACTERISTICS:
        (A) LENGTH: 315 amino acids
        (B) TYPE: amino acid
        (C) STRANDEDNESS: single
        (D) TOPOLOGY: linear (vii) IMMEDIATE SOURCE:
        (A) LIBRARY: GENBANK
        (B) CLONE: 189498

(xi) SEQUENCE DESCRIPTION: SEQ ID NO:3:

Met Ser Val Gly Phe Ile Gly Ala Gly Gln Leu Ala Phe Ala Lys Gly

-continued

```
  1               5              10              15
Phe Thr Ala Ala Gly Val Leu Ala Ala His Lys Ile Met Ala Ser Ser
             20              25              30
Pro Asp Met Asp Leu Ala Thr Val Ser Ala Leu Arg Lys Met Gly Val
             35              40              45
Lys Leu Thr Pro His Asn Lys Glu Thr Val Gln His Ser Asp Val Leu
             50              55              60
Phe Leu Ala Val Lys Pro His Ile Ile Pro Phe Ile Leu Asp Glu Ile
 65              70              75              80
Gly Ala Asp Ile Glu Asp Arg His Ile Val Val Ser Cys Ala Ala Gly
                 85              90              95
Val Thr Ile Ser Ser Ile Glu Lys Lys Leu Ser Ala Phe Arg Pro Ala
                100             105             110
Pro Arg Val Ile Arg Cys Met Thr Asn Thr Pro Val Val Val Arg Glu
             115             120             125
Gly Ala Thr Val Tyr Ala Thr Gly Thr His Ala Gln Val Glu Asp Gly
             130             135             140
Arg Leu Met Glu Gln Leu Leu Ser Thr Val Gly Phe Cys Thr Glu Val
145             150             155             160
Glu Glu Asp Leu Ile Asp Ala Val Thr Gly Leu Ser Gly Ser Gly Pro
                165             170             175
Ala Tyr Ala Phe Thr Ala Leu Asp Ala Asp Gly Gly Val Lys Met Gly
             180             185             190
Leu Pro Arg Arg Leu Ala Val Arg Leu Gly Ala Gln Ala Leu Leu Gly
         195             200             205
Ala Ala Lys Met Leu Leu His Ser Glu Gln His Pro Gly Gln Leu Lys
210             215             220
Asp Asn Val Ser Ser Pro Gly Gly Ala Thr Ile His Ala Leu His Val
225             230             235             240
Leu Glu Ser Gly Gly Phe Arg Ser Leu Leu Ile Asn Ala Val Glu Ala
             245             250             255
Ser Cys Ile Arg Thr Arg Glu Leu Gln Ser Met Ala Asp Gln Glu Gln
             260             265             270
Val Ser Pro Ala Ala Ile Lys Lys Thr Ile Leu Asp Lys Val Lys Leu
             275             280             285
Asp Ser Pro Ala Gly Thr Ala Leu Ser Pro Ser Gly His Thr Lys Leu
         290             295             300
Leu Pro Arg Ser Leu Ala Pro Ala Gly Lys Asp
305             310             315
```